(12) United States Patent
Rombouts et al.

(10) Patent No.: US 11,390,892 B1
(45) Date of Patent: Jul. 19, 2022

(54) HIGH YIELD LACTIC ACID PRODUCTION USING MIXED CULTURES

(71) Applicant: NATURE'S PRINCIPLES B.V., The Hague (NL)

(72) Inventors: Julius Laurens Rombouts, Delft (NL); Marinus Cornelius Maria Van Loosdrecht, Delft (NL); Robbert Kleerebezem, Delft (NL); David Gregory Weissbrodt, Delft (NL); Gerben Stouten, Delft (NL); Maximilienne Toetie Allaart, Delft (NL)

(73) Assignee: NATURE'S PRINCIPLES B.V., The Hague (NL)

(*) Notice: Subject to any disclaimer, the term of this patent is extended or adjusted under 35 U.S.C. 154(b) by 0 days.

(21) Appl. No.: 17/610,421

(22) PCT Filed: May 8, 2020

(86) PCT No.: PCT/EP2020/062951
§ 371 (c)(1),
(2) Date: Nov. 10, 2021

(87) PCT Pub. No.: WO2020/229370
PCT Pub. Date: Nov. 19, 2020

(30) Foreign Application Priority Data

May 10, 2019 (NL) ................................. 2023113

(51) Int. Cl.
*C12P 7/56* (2006.01)
*C12M 1/34* (2006.01)
*C12N 1/20* (2006.01)
*C12M 1/00* (2006.01)
*C12M 1/02* (2006.01)

(52) U.S. Cl.
CPC ............ *C12P 7/56* (2013.01); *C12M 29/18* (2013.01); *C12M 41/22* (2013.01); *C12M 41/26* (2013.01); *C12N 1/20* (2013.01)

(58) Field of Classification Search
CPC ........ C12P 7/56; C12M 29/18; C12M 41/22; C12M 41/26; C12N 1/20
USPC ........................................................ 435/139
See application file for complete search history.

(56) References Cited

U.S. PATENT DOCUMENTS

| 6,475,759 | B1* | 11/2002 | Carlson | C12N 1/00 |
| | | | | 435/252.9 |
| 2011/0210001 | A1* | 9/2011 | Xu | B01D 61/445 |
| | | | | 204/537 |
| 2015/0176035 | A1* | 6/2015 | Green | C12M 47/10 |
| | | | | 435/150 |

OTHER PUBLICATIONS

Akao et al., "Semi-Continuous L-Lactate Fermentation of Garbage Without Sterile Condition and Analysis of the Microbial Structure", Water Research, vol. 41, No. 8, Apr. 2007, pp. 1774-1780.
Amann et al., "Combination of 16S rRNA-Targeted Oligonucleotide Probes with Flow Cytometry for Analyzing Mixed Microbial Populations", Applied and Environmental Microbiology, vol. 56, No. 6, Jun. 1990, pp. 1919-1925.
Johnson et al., "Enrichment of a Mixed Bacterial Culture with a High Polyhydroxyalkanoate Storage Capacity", Biomacromolecules, vol. 10, No. 4, 2009, pp. 670-676.
Liang et al., "Lactic Acid Production from Potato Peel Waste by Anaerobic Sequencing Batch Fermentation Using Undefined Mixed Culture", Waste Management, vol. 45, Nov. 2015, pp. 51-56.
Partial International Search Report and Provisional Opinion; International Patent Application No. PCT/EP2020/062951 dated Oct. 14, 2020, 8 pages.
Rombouts et al., "Diversity and Metabolism of Xylose and Glucose Fermenting Microbial Communities in Sequencing Batch or Continuous Culturing", FEMS Microbiology Ecology, vol. 95, No. 2, 2019, 12 pages.
Tang et al., "Lactic Acid Fermentation from Food Waste with Indigenous Microbiota: Effects of pH, Temperature and High OLR", Waste Management, vol. 52, Jun. 2016, pp. 278-285.
Trebesius et al., "Culture Independent and Rapid Identification of Bacterial Pathogens in Necrotising Fasciitis and Streptococcal Toxic Shock Syndrome by Fluorescence in Situ Hybridisation", Med Microbiol Immunol, vol. 188, 2000, pp. 169-175.
Zhang et al., "Enhanced Isomer Purity of Lactic Acid from the Non-Sterile Fermentation of Kitchen Wastes", Bioresource Technology, vol. 99, No. 4, Mar. 2008, pp. 855-862.

\* cited by examiner

*Primary Examiner* — Jennifer M. H. Tichy
(74) *Attorney, Agent, or Firm* — AEON Law, PLLC; Adam L. K. Philipp; David V. H. Cohen

(57) ABSTRACT

The present invention is in the field of a method of producing lactic acid in high yield in a sequencing batch reactor. Therein glucose may be used as feedstock for bacteria, which ferment the glucose into lactic acid. The reactor is operated under at least partly defined non-axenic conditions and in a cyclic mode.

20 Claims, 2 Drawing Sheets

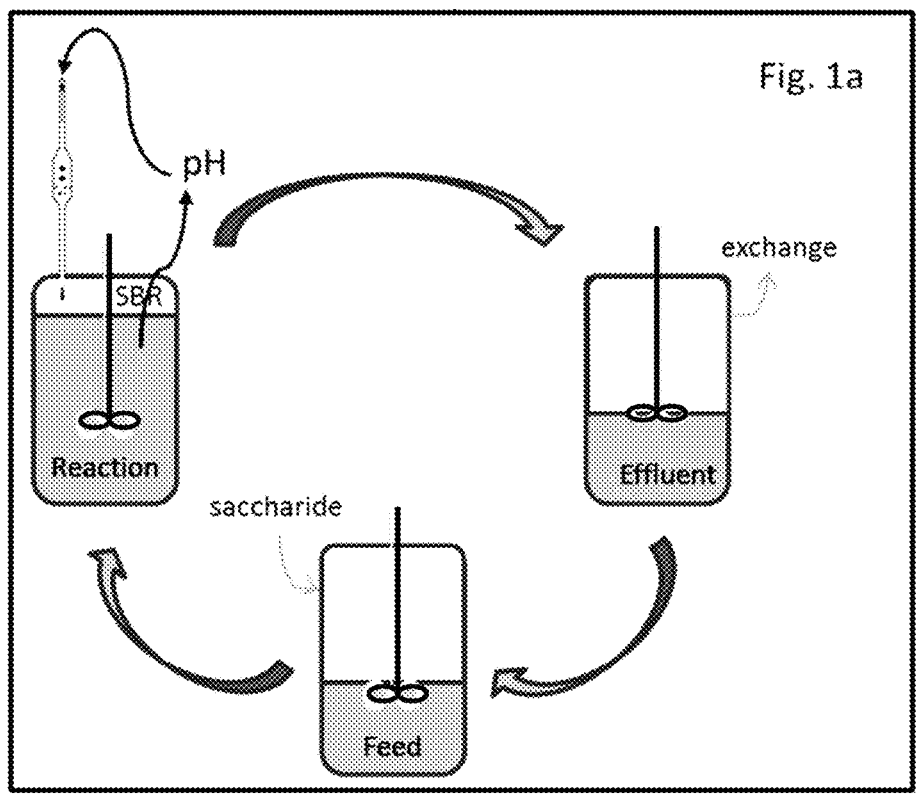
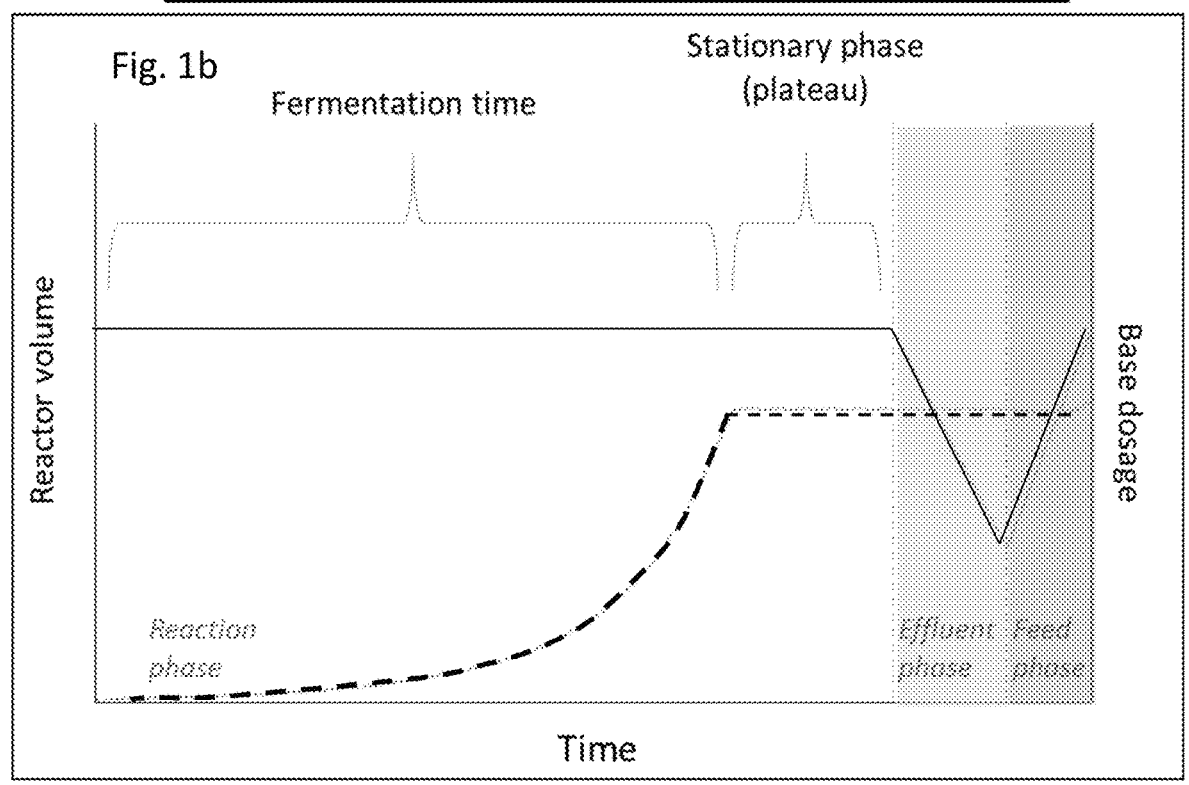

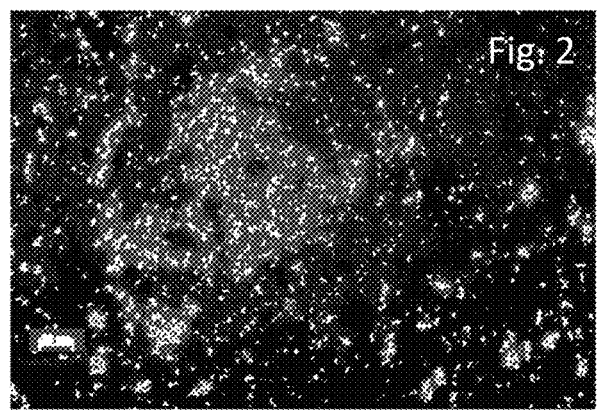
Fig. 2
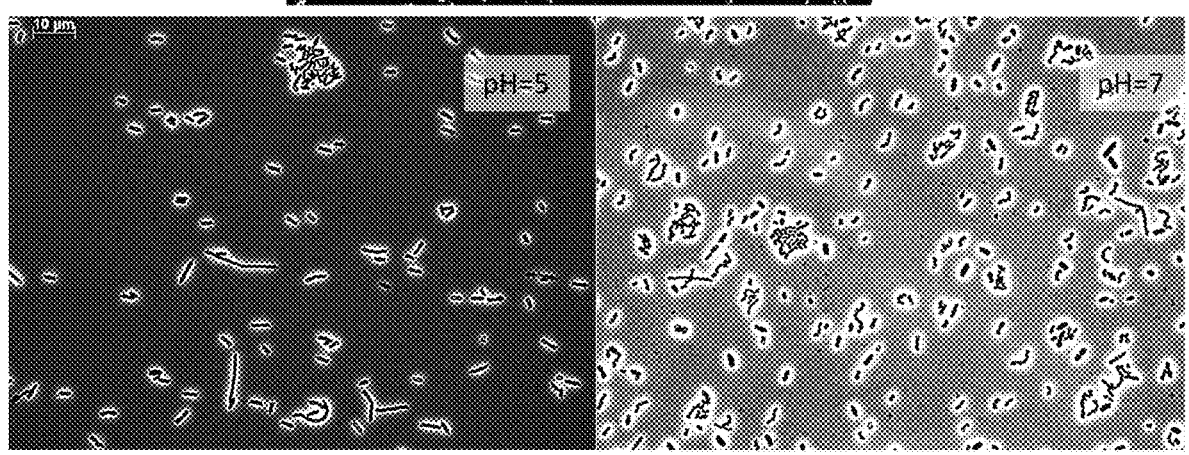
Fig. 3a
Fig. 3b
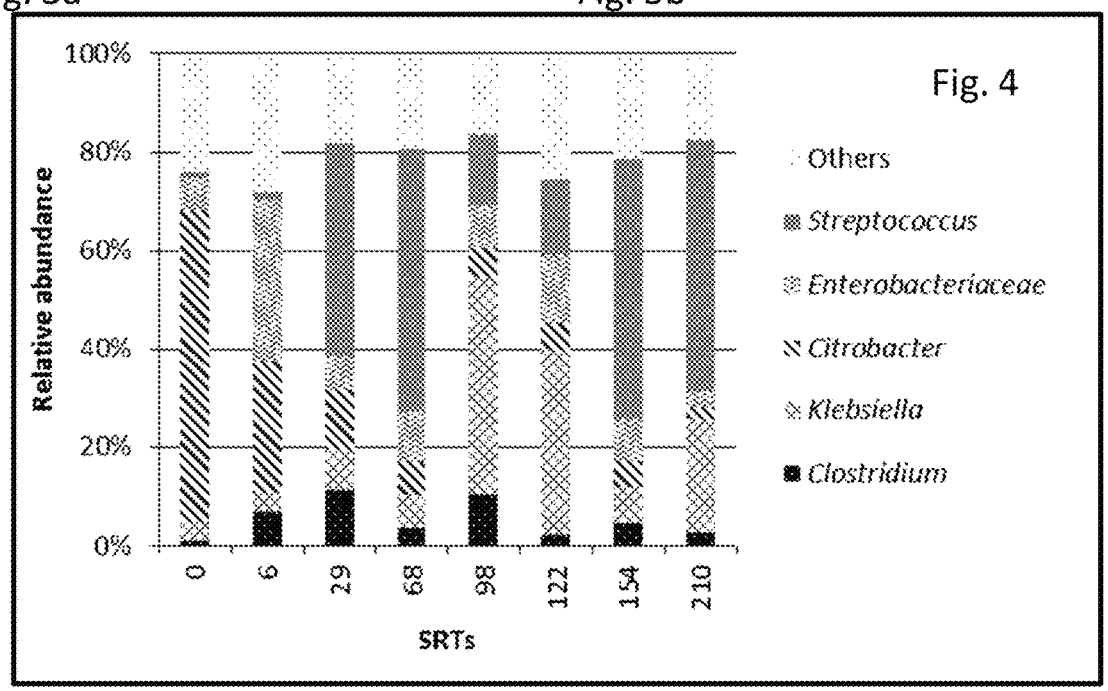
Fig. 4

HIGH YIELD LACTIC ACID PRODUCTION USING MIXED CULTURES

CROSS-REFERENCE TO RELATED APPLICATIONS

This application is a U.S. National Phase entry of, and claims priority to, PCT International Phase Application No. PCT/EP2020/062951, filed May 8, 2020, which claims priority to Dutch Patent Application No. NL 2023113, filed on May 10, 2019. The entire contents of the above-referenced applications and of all priority documents referenced in the Application Data Sheet filed herewith are hereby incorporated by reference for all purposes.

FIELD OF THE INVENTION

The present invention is in the field of a method of producing lactic acid in high yield in a sequencing batch reactor. Therein glucose or other sugars may be used as feedstock for bacteria, which ferment the glucose into lactic acid. The reactor is at least partly operated under defined conditions and in a cyclic mode.

BACKGROUND OF THE INVENTION

Lactic acid (CH3CH(OH)CO2H) is a simple organic chemical compound that can be used in many applications. It is a chiral molecule and it occurs as L- or D-lactic acid. It is noted that lactic acid is highly soluble.

Lactic acid fermentation is performed on an industrial scale by lactic acid bacteria (*Lactobacillus* species), which convert simple carbohydrates such as glucose, sucrose, or galactose to lactic acid, or by chemical synthesis. Lactic acid producing bacteria can produce two moles of lactate from one mole of glucose, or one mole of lactate from one mole of glucose as well as carbon dioxide and acetic acid/ethanol, which latter is not preferred.

Typically, lactic acid fermentation is performed under rather strict conditions. First of all, a relatively pure culture is used, such as *Lactobacillus delbrueckii*. The aqueous solution in which fermentation is performed is typically partly neutralized, such as with lime. Typically, a pH of about 4.5-5.0 is used. The fermentation temperature is >50° C. as production is often negligible up to 45° C. For fermentation typically a fermentor and seed reactor are used. In view of the pure culture sterilization of the feedstock and equipment used, e.g. the fermentor, is required. The yield of lactic acid is rather high, such as >0.9 lactic acid/g glucose (yield on carbon of 90%), the productivity is good (e.g. >5 g/l*h) and the titer relatively high (>150 g/l lactic acid).

These prior art methods are however costly. A pure culture may attribute to some 15% of production costs. The inoculum costs some 3%, and energy consumption some 4%. The fermentor is relatively large (a few thousand cubic meter), the seed reactor also has a significant volume (a few hundred cubic meters), and the need to be made from a relatively expensive material, such as stainless steel, making investments relatively high. As mentioned, proper sterilization is required, resulting in a down-time of the fermentor of some 20%, and high consumption of energy typically resulting in CO2 production. In unlucky cases a phage infection may occur, resulting in the loss of a batch of feedstock and the need to obtain a phage resistant strain, which can delay the production process. Quite often reactors and parts thereof need to be cleaned, which contributes to costs as well.

Some documents recite lactic acid production. Akao et al. In Water Research, Elsevier, Amsterdam, Vol. 41, No. 8, Mar. 23, 2007, p. 1774-1780 recites a method for producing L-lactate by semi-continuous fermentation of garbage without sterile conditions. Tang Jialing et al., in Waste Management, Elsevier New York Vol. 52, Mar. 31, 2016, p. 278-285 recites a method for producing lactic acid in a sequence batch fermentation of a garbage feedstock. Background art can be found in Liang et al., Waste management, Vol. 45, Nov. 1, 2015, p. 51-56, Zhang et al., in Bioresource Technology, Elsevier Amsterdam, Vol. 99, No. 4, Mar. 1, 2008, p. 855-862, and US 2011/210001 A1.

Lactic acid is a precursor for polylactic acid (PLA), which can be atactic or syndiotactic, and which polymers are biodegradable polyesters. Lactic acid may also be used as a food conservative, in cosmetics, and as a pharmaceutical component. The market size for lactic acid is huge (>5 M€/year) and growing. Therefore, there is a need for an efficient method of producing lactic acid.

The present invention therefore relates to an improved method of producing lactic acid by fermentation, which solves one or more of the above problems and drawbacks of the prior art, providing reliable results, without jeopardizing functionality and advantages.

SUMMARY OF THE INVENTION

It is an object of the invention to overcome one or more limitations of the methods and devices of the prior art and at the very least to provide an alternative thereto. In a first aspect the present invention relates to a method of producing lactic acid in a sequencing batch reactor comprising adaptively cycling (see e.g. FIG. 1*b*) at least once between (i) a reaction phase, (ii) an effluent phase, and (iii) a feed phase, preferably 2-5000 times adaptive cycling, more preferably 4-1000, such as 5-1000 times. Each phase is considered to relate to a period of time. By coupling base dosing to substrate consumption and by closely monitoring a base consumption an adaptive cycle can be ended almost immediately when completed, consumption of substrate (e.g. glycose) is as fast as possible, resulting in high time-averaged volumetric rates. Typically, 1-20 adaptive cycles per day are possible, such as 2-10 adaptive cycles. Operation of the reactor can be continued for long periods of time. Maintenance can be performed 1-4 times per year, or less. The present method uses a mixed culture capable of fermenting saccharide into lactic acid, which is added, such as to the reactor. Compared to prior art methods as described above the present method is considered to be >20% cheaper in terms of unit production costs of lactic acid. Some reasons thereto are that no sterilization is needed, no pure culture, such as a *Lactobacillus delbrueckii* culture, is required, no inoculum reactor and seed reactor are needed, the size of the present reactor can be a factor smaller and still having a similar production rate, the present method provides a high start biomass enabling a high productivity, such as >6 g/l*h, the possibility of reusing biomass as protein and vitamin source therewith reducing peptide and vitamin source consumption, the (indirect) production of CO2 is reduced significantly, scheduled down-time is low as no sterilization is required, and unscheduled down time, such as due to phage infection, is very unlikely due to the mixed culture comprising multiple strains and species. The biomass may be recycled, especially as it may be still intact, and therewith contributing to an increase in productivity and yield. In addition, the throughput is higher. The downside is that somewhat lower yields (70% versus 90%) are obtained, which may be due to more biomass and possible byproduct, and in general there is no direct control over D/L ratio lactic acid; however, under specific conditions the latter can be resolved. Surprisingly at a pH of about 7 no detectable D-lactic acid (<0.1%) is formed and >99.9% L-lactic acid.

Important differences between the present invention and background art are that in the prior art the impact of the presence or absence of proteins has not been specifically addressed as enhancing the lactic acid yield and productivity. Only the amount of carbohydrate and protein are quantified. Also, the presence or absence of B vitamins in the feedstock is not mentioned. And most importantly, none of the references demonstrate an "adaptive cycling" process. These are considered as the most unique parts of the invention, with the other factors enhancing the effectiveness of the invention.

The present method comprises a reaction phase wherein (ia1) maintaining the pH at a predetermined level between 5.6 and 8.5, preferably between 5.9 and 8.0, more preferably between 6.4 and 7.5, such as at 7.0, which is compared to prior art methods relatively high, (ia2) maintaining the temperature at 30-80° C., preferably at 32-72° C., more preferably at 35-63° C., even more preferably at 37-60° C., such as 38-50° C., e.g. 40-45° C., which preferred range is compared to prior art methods relatively low, (ia3) stirring the reaction phase, such as at 1-600 rpm, (ib) adding a base when the pH is below the predetermined level until the pH is at or above the predetermined level. The pH can be measured directly with a simple pH sensor. (ic1) Allowing fermentation to continue during a fermentation time until fermentation reaches a stationary phase, which stationary phase can be determined as then fermentation substantially stops, and as a consequence the pH remains more or less constant, such as wherein the pH is substantially constant during at least 10 minutes, and no further base need to be added. So e.g. by monitoring an amount of base added over time, the stationary phase can be determined adequately, albeit with a small delay in time. (ic2) When fermentation has reached the stationary phase removing part of the effluent to the effluent phase, and (ic3) adding feed to the reaction phase, therewith largely or fully replenishing the reaction phase. The feed can be added subsequently to removing effluent from the reaction phase, during reaction, before reaction, and combinations thereof. In the effluent phase (iia) at least part of the lactic acid is removed, and (iib) preferably a remainder of the effluent phase is provided to the feed phase, preferably wherein 30-70% of broth is provided to the feed phase, such as 40-60% of broth. The lactic acid may be remover through an outlet towards a vessel or the like, it may be precipitated in the reactor, such as by adding Ca2+, it may be separated over a membrane, and combinations thereof. So, a part of the broth may be recycled. In an alternative, or in addition, lactic acid may be removed from the reaction phase, such as by in-situ separation. In the feed phase (iiia) an aqueous feed mixture is provided comprising >10 g/l of a saccharide comprising compound, wherein the saccharide compound is selected from glucose, sucrose, fructose, galactose, lactose, disaccharides, oligo saccharides, poly saccharides, such as with 3-100 saccharides, starch, inulin, preferably wherein the saccharide comprising compound is a single compound, such as solely glucose, and >1 g peptide/100 g saccharide compound, or a combination thereof, wherein the peptide concentration in the feed phase is between 1-30 g peptide/100 g saccharide. It has been found that in addition to a saccharide as basic feed compound also peptides are required in order to obtain sufficient yield. Without the amount of peptide mentioned the yield drops to some 10%, much lower than the present 70% typically obtained. When starting the at least one adaptive cycle a mixed starting culture is added, at the start of the reaction phase, which is capable of fermenting saccharide into lactic acid, such as added into the reactor. A biomass hydraulic retention time is controlled between 4 h-144 h, such as between 1-8 days. It is noted that the solid retention time and hydraulic retention time may be substantially the same, especially when continuous mixing is applied during volume exchange, such as during effluent removal. The HRT is considered to depend on cycling time, which is controlled by the adaptive cycling.

In a second aspect the present invention relates to an apparatus for performing a method according to the invention, which may be a relatively cheap apparatus, such as a plastic or concrete apparatus, comprising a feed container, the feed container having a volume of 1-50 m$^3$, the feed container being in fluidic contact with a reactor over a feed valve, the reactor having a pH-sensor in fluidic contact with the aqueous solution of the reactor, a reservoir comprising a base and a reservoir valve and optionally a pump, the reactor having a volume of 10-100 m$^3$, the reactor being in fluidic contact with an effluent container over an effluent valve, the effluent container having a volume of 1-50 m$^3$, and the effluent container being in fluidic contact with the feed container, each container and reactor having a mixer for rotating an aqueous phase with 1-600 rpm, the effluent container having an outlet for removing lactic acid, and the feed container having an input for replenishing feed, and a controller adapted (a) to open the reservoir valve when the pH drops below a predetermined level and to close said reservoir valve when the pH has reached said predetermined level again, (b) to open the feed valve when the fermentation reaches a stationary phase and to add feed, (c) to open the feed valve when the effluent has been partly removed and to add feed to replenish the reactor, and (d) to open the effluent valve when effluent is removed, such as when the liquid in the reactor has reached a predetermined volume.

The present invention provides a solution to one or more of the above-mentioned problems and overcomes drawbacks of the prior art.

Advantages of the present description are detailed throughout the description.

DETAILED DESCRIPTION OF THE INVENTION

In an exemplary embodiment of the present method biomass may be adaptive cycled at least once between the reaction phase, the effluent phase, and the feed phase. It has been found that biomass not only contributes to fermentation of saccharide into lactic acid, but also provides peptides, therewith improving the yield and throughput.

In an exemplary embodiment of the present method the feed phase may comprise >80 g/l saccharide compound, such as 100-200 g/l.

In an exemplary embodiment of the present method the peptide concentration in the feed phase is between 1-40 g peptide/100 g saccharide, preferably between 2-30 g/100 g, more preferably between 5-15 g/100 g.

In an exemplary embodiment of the present method the peptide may be selected from monopeptides, dipeptides, tripeptides, tetrapeptides, or is provided as microbial biomass, and combinations thereof. In an example of biomass also peptides in yeast extract, or whey, or by-product of biological origin may be used. And further the biomass in the present system may be recycled, providing peptides, as well as vitamins or precursors thereof.

In an exemplary embodiment of the present method a reactor size may be 50-1000 m³, such as 100-300 m³. Such is much smaller than prior art reactors, therewith significantly reducing energy consumption in the production process, such as die to agitation (stirring) of the reaction phase.

In an exemplary embodiment of the present method the reactor may be a sequencing batch reactor or a sequencing fed batch rector. The present reactor may relate to a reactor comprising at least one of a zone of an apparatus, a phase of operation of an apparatus, and a sub-reactor. The sequencing in combination with adaptive cycling provides a quick start up, high throughput, and good adaptability of the system to potential varying characteristics.

In an exemplary embodiment of the present method no sterilization needs to be carried out.

In an exemplary embodiment of the present method no inoculation needs to be carried out.

In an exemplary embodiment of the present method no live yeast is present in the feed phase stock.

The above relate to a significant reduction in costs of operation, simplified mode of operation, reduced downtime, and reduced risk of infections.

In an exemplary embodiment of the present method the feed phase may comprise a vitamin B and/or metabolic precursor thereof, preferably $10^{-2}$-10 mg vitamin B/g saccharide and/or precursor, preferably $2*10^{-2}$-5 mg/g vitamin B and/or precursor, such as 0.05-1 mg/g. It has been found that these vitamin and precursors improve the yield significantly.

In an exemplary embodiment of the present method the vitamin B may be selected from vitamin B1 (thiamine), vitamin B2 (riboflavin), vitamin B3 (niacin, nicotinamide, nicotinamide riboside), vitamin B5 (pantothenic acid), vitamin B6 (pyridoxine), vitamin B7 (biotin), vitamin B12 (cobalamin), a salt thereof, such as a phosphate salt, and combinations thereof.

In an exemplary embodiment of the present method the precursor may be selected from metabolic precursors for coenzyme in catabolism of sugar, co-factor FAD, co-factor FMN, coenzyme NAD, coenzyme NADP, coenzyme A, a metabolic coenzyme, a fatty acid metabolism coenzyme, an amino acid metabolism coenzyme, and combinations thereof.

In an exemplary embodiment of the present method a culture titer of lactic acid of >40 g/l may be maintained, typically >50 g/l, such as >100 g/l, that is high titers are obtainable.

In an exemplary embodiment of the present method a magnesium (cation) concentration in the feed phase may be 0.1-5 g/l, such as 0.2-2 g/l.

In an exemplary embodiment of the present method a calcium (cation) concentration in the feed phase may be >1.5 mg Ca/g saccharide. So, for 10-200 g saccharide/l more than 1.5-300 mg Ca/L may be provided.

The magnesium and calcium, typically provided as $Mg^{2+}$ ion and $Ca^{2+}$ ion, are found to contribute to fermentation.

In an exemplary embodiment of the present method the mixed culture may be enriched, such as by increasing an amount of saccharide compound, e.g. to >100 g/l, such as >200 g/l.

In an exemplary embodiment of the present method a biomass retention time may be controlled, such as between 1-8 days.

In an exemplary embodiment of the present method the reaction phase comprises >10% *Streptococcus*, such as >50% *Streptococcus*, which can be determined by a semi-quantitative method like fluorescent in situ hybridization, or with any other method, such as with PCR.

In an exemplary embodiment of the present method a hydraulic retention time (HRT) may be from 1-8 days, preferably between 18-96 hours, such as 24-48 hours.

In an exemplary embodiment of the present method a base may be selected from hydroxides, oxides, ammonia, and combinations thereof, preferably comprising $Ca^{2+}$, $Na^+$, or $Mg^{2+}$, and combinations thereof.

In an exemplary embodiment of the present method a pH may be maintained at 7.0±0.5, a temperature at 30-55° C., a peptide amount at >2 g/100 g saccharide, a vitamin B at >0.1 g/l, and wherein >98% L-lactic acid is produced, such as >99.9% L-lactic acid (on a mol lactate/mol saccharide comprising compound basis). This is rather surprising that virtually no D-lactic acid is produced, and substantially only L-lactic acid.

The invention will hereafter be further elucidated through the following examples which are exemplary and explanatory of nature and are not intended to be considered limiting of the invention. To the person skilled in the art it may be clear that many variants, being obvious or not, may be conceivable falling within the scope of protection, defined by the present claims.

SUMMARY OF THE FIGURES

FIGS. 1*a-b*, 2, and 3*a-b* and 4 show some details of the present invention.

DETAILED DESCRIPTION OF FIGURES

In FIG. 1*a* a schematic representation of the present adaptive cycle is shown. A feed phase is provided with a saccharide, and typically mixed. The feed is provided, in an adaptive cyclic mode, to a reaction phase, wherein microorganisms produce lactic acid from the saccharide. In the reaction phase the pH is measured. Upon decrease of the pH a source of base is activated, and base is added until the pH reaches a predetermined level. Then the addition of base is stopped, for the time being. The effluent of the reaction phase is transferred to an effluent phase, and the lactic acid is removed. A remainder of the effluent phase is fed back to the feed phase.

Initially base is added to the reaction phase, in order to compensate the pH for the lactic acid being formed. The amount of base over time decreases, until a plateau is reached. Then addition of base is stopped, as no further lactic acid is formed. The reactor volume as function of time/phase of operation is shown. Phases in a single adaptive cycle and theoretical associated base dosage profiles of the sequencing batch reactor used to perform adaptive base adaptive cycling. The adaptive cycle length was controlled by imposing a maximum base constant time, after which a new adaptive cycle was initiated, starting from the effluent phase.

FIG. 2: Result of a FISH image using the str probe (light grey), specific for the *streptococcus* genus (Trebesius et al. 2000) compared to the EUB338 probe mix (dark grey) (Amann et al. 1990).

FIGS. 3*a-b* show microscopic images of bacterial cultures at pH=5 (left) and pH=7 (right), clearly showing that different bacteria are present at the higher pH.

FIG. 4: Development of the read abundance of the 16S rRNA gene V3-V4 region in time on genus level. Various species are found, which develop over time in amount.

*Streptococcus, Enterobacteriaceae, Citrobacter, Klebsiella,* and *Clostridium* are found in relatively high amount.

EXAMPLES

Materials and Methods
Reactor Operation

The enrichment was carried out in a 3 L bioreactor with a working volume of 2 L. Anaerobic conditions were maintained by continuously sparging the reactor with N2 at a rate of 216 mL min-1 (@T=273K, P=105 kPa). The culture was taken out of the reactor for biofilm removal from reactor walls and head three times per week. The reactor was continuously agitated at a speed of 300 rpm using mechanical stirrers. Reactor temperature was maintained at 30°C by recirculating water heated at 31° C. (E300 thermostat, Lauda, Germany) in the outer wall of the reactor. To prevent culture broth evaporation, the off-gas was cooled using a cryostat set to 5° C. Reactor pH was maintained at 5.0±0.2 using 8 mol $L^{-1}$ NaOH and 1 mol $L^{-1}$ HCl solutions (ADI 1030 Bio controller, Applikon, The Netherlands). To prevent excessive foaming, anti-foaming agent (3% v:v anti-foam C, Sigma Aldrich, Germany) was added in equal amounts and at equal speed as NaOH during 10 g $L^{-1}$ glucose fermentations.

Enrichment Medium

The enrichment at 10 g $L^{-1}$ glucose was performed using a medium to which $NH_4Cl$, $KH_2PO_4$ and $FeCl_2.4H_2O$ were added to obtain a set molar C:N:P:Fe ratio of 100:5:1:0.33 and 1.5 g yeast extract was added per 10 g of glucose. Glucose and yeast extract solutions were autoclaved separately at 110° C. for 20 minutes and then combined. Salts were supplied to the reactor from a second vessel, which was autoclaved at 121° C. Magnesium concentrations were adjusted to increasing glucose concentrations. Trace elements were supplied in sufficient amounts.

SBR Phases and Start-Up

The reactor was operated in SBR mode. In a start-up phase for culture development the reactor was operated in batch mode until glucose was entirely consumed. For inoculation of the enrichment, 10 mL (0.5% v/v) of suspended and sieved (150 μm filtered) soil from the botanical garden of TU Delft was used (pH 7.4) and 10 mL of anaerobic digester sludge (Harnaschpolder, The Netherlands). After the start-up phase the SBR mode with an exchange ratio of 50% was entered. Three different SBR phases are distinguished: the effluent phase (5 minutes), the feed phase (4 minutes) and the reaction phase. The length of the reaction phase was dependent on the speed of microbial conversions in the reactor: adaptive base adaptive cycling was used to control the adaptive cycle time (FIG. 1). The base constant time was initially kept at 90 minutes to avoid biomass washout, as an initial lag phase was observed in the adaptive cycles at the start of the enrichment. Throughout the enrichment, the base constant time was gradually decreased to 20 minutes.

Batch with 100 g $L^{-1}$ Glucose at pH 5

Anaerobicity, temperature, pH, agitation and broth evaporation were controlled as described for the sequencing batch reactors. After 2.5 days of operation the reactor was spiked with 0.25 times the initial amount of trace elements.

Samples for monitoring biomass growth (OD660), glucose consumption and product formation were taken every 30 minutes for the first 2.5 hours of the cultivation. After this, samples were taken every hour until t=8 h and finally 3 samples per day were taken. The final biomass concentration was calculated by measuring the volatile suspended solids (VSS) at the end of the fermentation.

SBR Operation at pH 7

The enrichment at pH 7 was carried out as described for pH 5, but the pH was controlled at 7.2±0.2 using 8 mol $L^{-1}$ NaOH. The reactor was inoculated with 5 mL suspended and sieved soil and 5 mL anaerobic digester sludge. Adaptive base adaptive cycling with a minimal base constant time of 10 minutes was used for the first two weeks of enrichment, after which a fixed adaptive cycle length of 90 minutes was set. Initially, the culture broth was agitated at 300 rpm. However, after 145 SRTs the stirring speed was increased to 600 rpm to improve mass transfer of carbon dioxide to the gas phase.

Batch with 100 g $L^{-1}$ Glucose at pH 7

The batch reactor was operated as described for the batch process at pH 5. The reactor was inoculated with cell pellets of approximately 1 L of the culture obtained at the end of the enrichment at pH 7. Samples were taken every 30 minutes for the first 3.5 hours and every hour until glucose was nearly depleted (<16 mM residual glucose). Anti-foam was added manually when foaming occurred. Culture was stored in the fridge overnight before collecting the pellet for VSS determination.

Analytical Methods

The gas productivities ($H_2$ and $CO_2$) and acid/base dosages for pH control were monitored on-line using MFCS software (Sartorius, Germany) and a Rosemount Analytical NGA 2000 (Emerson, USA). Biomass concentrations were monitored both by measuring optical density (OD660) and the amount of VSS in the broth as described earlier using 150 mL effluent (APHA/AWWA/WEF 1999), calculated assuming a biomass molecular weight of 24.6 g $mol^{-1}$. Both OD and VSS were always determined in duplicate. Glucose, ethanol and VFA concentrations were determined using high performance liquid chromatography (HPLC) using an Aminex HPX-87H column (BioRad, USA) at 59° C. coupled to a refractive index- and ultraviolet detector (Waters, USA). 1.5 mmol $L^{-1}$ phosphoric acid was used as eluent. Biomass was removed from the reactor samples by centrifugation and filtration using a 0.22 μm membrane filter (Millipore, Millex-GV, Ireland).

Microbial Community Analysis

DNA was extracted from cell pellets from different time points in the enrichment using the DNAeasy microbial extraction kit (Qiagen Inc., Germany) following manufacturer's instructions and sent to Novogene (Hong Kong, China) for 16S rRNA amplicon sequencing of the V3-V4 region as described by Rombouts et al., (2019).

Fluorescent in situ hybridization (FISH) was used for analyzing the microbial community with epifluorescence microscopy (Axioplan 2 imaging, Zeiss, Germany). Fixation and overnight hybridization were performed as described by Johnson et al. (2009) using the probes listed in table 1. An additional DAPI staining targeting all microbial cells was used by incubating the slides for 15 minutes with 10 μL of 10 mg $mL^{-1}$ DAPI solution after washing and drying.

| Microorganism | Probe | Formamide (%) | Sequence (5' → 3') |
| --- | --- | --- | --- |
| Eubacteria | EUB338 | 5-30 | GCTGCCTCCCGTAGGAGT |

-continued

| Microorganism | Probe | Formamide (%) | Sequence (5' → 3') |
|---|---|---|---|
| Lactobacillus | Lacto772 | 25 | YCACCGCTACACATGRAGTTCCACT |
| Lactococcus | Lactococcus4 | 5 | CTGTATCCCGTGTCCCGAAG |
| Megasphaera | Mega-X | 25 | GACTCTGTTTTTGGGGTTT |
| Streptococcus | Str | 30 | CAC TCT CCC CTT CTG CAC |
| Enterobacteriaceae | Ent183 | 20 | CTC TTT GGT CTT GCG ACG |

Results

A product spectrum was monitored in time of both enrichments. Lactate was the main fermentation product in both conditions. At 30 SRTs, the amount of trace elements was doubled, leading to mainly lactate production. At pH 7, a 5.4 times higher productivity was reached. What is very surprising is that only L-lactic acid is produced at pH 7, while a nearly racemic mixture is produced at pH 5.

| | | pH 5 | pH 7 |
|---|---|---|---|
| 10 g L$^{-1}$ glucose | Maximum obtained lactate yield ($g_p$ $g_s^{-1}$) | 0.76 | 0.69 |
| | Maximum obtained productivity (g L$^{-1}$ h$^{-1}$) | 1.16 | 6.24 |
| | Ratio D:L - lactate | 53:47 | 1:99 |
| | $Y_{x/s}$ (Cmol$_x$ Cmol$_s^{-1}$) | 0.14 | 0.20 |
| | $q_s$ (Cmol$_s$ Cmol$_x^{-1}$ h$^{-1}$) | 0.74 | 2.25 |
| | $\mu_{average}$ (h$^{-1}$) | 0.11 | 0.46 |
| 100 g L$^{-1}$ glucose | $Y_{LA/s}$ ($g_p$ $g_s^{-1}$) | 0.60 | 0.59 |
| | Final attained lactate concentration (g L$^{-1}$) | 57.6 | 56.6 |
| | $Y_{x/s}$ (Cmol$_x$ Cmol$_s^{-1}$) | 0.09 | 0.14 |
| | Average productivity (g L$^{-1}$ h$^{-1}$) | 0.73 | 4.72 |

The microbial community analysis revealed that the pH enrichment was predominated by *Lactobacillus* species. A significant side population of Megasphaera was detected.

At pH 7, *Streptococcus* was observed to be predominant genus, with also several Enterobacteriaceae genera occurring, such as *Klebsiella* and *Citrobacter*. The amount of *Streptococcus* was shown to be very dominant, in the range of >90% of the biomass.

CONCLUSIONS

Obtaining selective L-lactic acid production using mixed cultures without sterilisation and a pure culture inoculum was achieved. An acidic environment at pH 5 was tested in comparison to a neutral pH environment at pH 7 under the same cultivation conditions. A complex medium was used, as this stimulates the growth of lactic acid bacteria. The adaptive cycle times could be adjusted to the time base dosage stopped and the substrate, glucose, was assumed to be depleted (the 'plateau' was reached). It was found that lactic acid bacteria could be successfully enriched at both pH 5 and pH 7 using the described enrichment strategy. Further, lactic acid production at pH 7 is favoured over pH 5, as the productivity is higher and there is selective production of L-lactic acid.

Inventors have obtained a high yield of lactic acid on glucose using a defined medium and defined bioreactor conditions. A stable yield of >70% LA g/g of glucose, and a productivity of 6.2 g/l*h in a 2l bioreactor at 10 g/l glucose and a titer of lactic acid of 57 g/l is obtained in the reactor. These conditions, or more explicitly, these ecological parameters, can be applied to optimize current large-scale fermentations producing lactic acid. Also, current waste streams can be used to ferment these to lactic acid at high yield and refine the lactic acid out of the stream.

With the present method and system, a maximum obtained yield of 0.69 (molp mols$^{-1}$), a maximum obtained productivity of 6.24 (g L$^{-1}$ h$^{-1}$), a ratio D:L-lactate of 0-100, and a final attained lactate concentration of 56.6 (g L$^{-1}$) were obtained.

Below results of prior art documents and the present invention are compared.

Table best achieved results on the basis of yield

| Parameter | Present invention | Akao et al. 2007 | Tang et al. 2016 | Liang et al. 2015 | Zhang et al. 2008 |
|---|---|---|---|---|---|
| pH | 7.0 | 6 | pH to 6 every 12 hours | Uncontrolled, around 3.5 | 7 |
| Temperature | 30° C. | 55° C. | 37° C. | 35° C. | 35° C. |
| HRT and SRT | 34 hours | 240 hours | 120 hours | 24 hours | 120 hours |
| Ratio peptides/carbohydrates (g/100 g) | 7 | 31.4 | 10.9 | 56.1 | 25.2 |
| Carbohydrate concentration feed (g L$^{-1}$) | 100 | 83 | 56.8 | 11.97 | 99.14 |
| Yield lactic acid on carbohydrate (g/g) | 0.82 | 0.73 | 0.54 | 0.63 | 0.65 |
| Productivity (g LA L$^{-1}$ h$^{-1}$) | 2.42 | 0.33 | 0.25 | 0.16 | 0.53 |
| Lactic acid concentration at the end of the experiment, product titer (g L$^{-1}$) | 82.3 | 39.6 | 30.5 | 7.5 | 64 |
| Ratio D:L | 1:99 | 3:97 | Not reported | Not reported | 40:60 |

Further tests have been performed, using 100 g/l glucose producing 82 g/l lactate, with a L:D ratio of 1:99. The biomass yield was 0.08 Cmol-x/Cmol-S and a productivity of 2.35 g/L/h was obtained.

So for the best results it is noted that Akaou used a different temperature, with still lower yield and much lower productivity, Tang sets the pH to 6 every 12 hours, which has nothing to do with controlling, and Liang has an uncontrolled pH. Yields of lactic acid are much lower, and productivity is a factor lower, and typically almost an order lower. Also the D:L ratio is much better.

The invention claimed is:

1. A method of producing lactic acid in a sequencing batch reactor comprising:
adaptively cycling at least once between (i) a reaction phase, (ii) an effluent phase, and (iii) a feed phase, wherein
in the reaction phase:
(ia1) maintaining the pH at a predetermined level between 5.6 and 8.5,
(ia2) maintaining the temperature at 30-80-° C.,
(ia3) stirring the reaction phase,
(ib) adding a base when the pH is below the predetermined level until the pH is at or above the predetermined level,
(ic1) allowing fermentation to continue during a fermentation time until fermentation reaches a stationary phase wherein the pH is constant during at least 10 minutes,
(ic2) when fermentation has reached the stationary phase removing part of a produced effluent to the effluent phase, and
(ic3) adding feed to the reaction phase,
in the effluent phase:
(iia) removing at least part of produced lactic acid from the effluent, and
in the feed phase:
(iiia) providing an aqueous feed mixture comprising:
>10 g/l of a saccharide comprising compound, wherein the saccharide compound is selected from glucose, sucrose, fructose, galactose, lactose, disaccharides, oligo saccharides, poly saccharides, starch, inulin, or a combination thereof, and
>1 g peptide/100 g saccharide compound, wherein the peptide concentration in the feed phase is between 1-30 g peptide/100 g saccharide,
adding, at a start of the reaction phase, a mixed starting culture capable of fermenting the saccharide into lactic acid, and
wherein a biomass hydraulic retention time is controlled to between 4-144 hours.

2. The method according to claim 1, wherein microbial biomass is cycled at least once between the reaction phase, the effluent phase, and the feed phase.

3. The method according to claim 1, wherein the feed phase comprises >80 g/l saccharide compound.

4. The method according to claim 1, wherein the peptide concentration in the feed phase is between 2-20 g peptide/100 g saccharide.

5. The method according to claim 1, wherein the peptide is selected from monopeptides, dipeptides, tripeptides, tetrapeptides, is provided as microbial biomass, is provided as recycled microbial biomass, and combinations thereof.

6. The method according to claim 1, wherein a reactor size is 50-1000 $m^3$.

7. The method according to claim 1, wherein the sequencing batch reactor is a sequencing fed batch reactor.

8. The method according to claim 1, wherein no sterilization is carried out, no inoculation is carried out, and/or no live yeast is present in feed phase stock.

9. The method according to claim 1, wherein the feed phase comprises vitamin B and/or a metabolic precursor thereof.

10. The method according to claim 9, wherein the vitamin B is selected from vitamin B1, vitamin B2, vitamin B3, vitamin B5, vitamin B6, vitamin B7, vitamin B12, a salt of said vitamins, and combinations thereof.

11. The method according to claim 9, wherein the metabolic precursor is selected from metabolic precursors for coenzyme in catabolism of sugar, cofactor FAD, cofactor FMN, coenzyme NAD, coenzyme NADP, coenzyme A, a metabolic coenzyme, a fatty acid metabolism coenzyme, an amino acid metabolism coenzyme, and combinations thereof.

12. The method according to claim 1, wherein a culture titer of lactic acid of >40 g/l is maintained during the reaction phase.

13. The method according to claim 1, wherein a magnesium cation concentration in the feed phase is 0.1-5 g/l, and/or wherein a calcium cation concentration in the feed phase is >1.5 mg Ca/g saccharide compound.

14. The method according to claim 1, wherein the mixed starting culture is enriched for L-lactic acid producing microorganisms.

15. The method according to claim 1, wherein a biomass hydraulic retention time is controlled to between 18-96 hours.

16. The method according to claim 1, wherein the reaction phase comprises >10% Streptococci.

17. The method according to claim 1, wherein a hydraulic retention time (HRT) is from 1-8 days.

18. The method according to claim 1, wherein the base is selected from hydroxides, oxides, ammonia, and combinations thereof.

19. The method according to claim 1 wherein the pH is maintained at 7.0±0.5, the temperature is maintained at 30-55° C., the peptide concentration is >2 g/100 g saccharide compound, a vitamin B is present at >0.1 g/l, and wherein >98% L-lactic acid is produced on a mol lactate/mol saccharide compound basis.

20. The method according to claim 1, further comprising (iib) providing a remainder of the effluent phase to the feed phase.

* * * * *